United States Patent
Lui et al.

(10) Patent No.: US 9,932,312 B2
(45) Date of Patent: Apr. 3, 2018

(54) PROCESS FOR PREPARING 5-FLUORO-1-METHYL-3-DIFLUOROMETHYL-1H-PYRAZOLE-4-CARBALDEHYDE

(71) Applicant: BAYER CROPSCIENCE AG, Monheim (DE)

(72) Inventors: Norbert Lui, Odenthal (DE); Sergii Pazenok, Solingen (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/760,674

(22) PCT Filed: Jan. 16, 2014

(86) PCT No.: PCT/EP2014/050767
§ 371 (c)(1),
(2) Date: Jul. 13, 2015

(87) PCT Pub. No.: WO2014/111449
PCT Pub. Date: Jul. 24, 2014

(65) Prior Publication Data
US 2015/0353502 A1    Dec. 10, 2015

(30) Foreign Application Priority Data

Jan. 17, 2013  (EP) .................... 13151564

(51) Int. Cl.
*C07D 231/16*    (2006.01)
(52) U.S. Cl.
CPC .................. *C07D 231/16* (2013.01)
(58) Field of Classification Search
CPC .................................................. C07D 231/16
See application file for complete search history.

(56) References Cited

U.S. PATENT DOCUMENTS

| 8,765,971 B2 * | 7/2014 | Pazenok | C07D 231/16 548/366.1 |
| 2009/0306401 A1 * | 12/2009 | Neeff | B01J 31/0237 548/374.1 |
| 2010/0096585 A1 * | 4/2010 | Zierke | C07C 17/208 252/182.12 |
| 2011/0207940 A1 * | 8/2011 | Pazenok | C07D 231/16 548/366.1 |
| 2012/0065164 A1 | 3/2012 | Bartels et al. | 514/63 |
| 2013/0165664 A1 | 6/2013 | Pazenok et al. | 548/366.1 |

FOREIGN PATENT DOCUMENTS

| WO | WO 2010/130767 A2 | 5/2010 | |
| WO | WO 2011/061205 A1 | 5/2011 | |
| WO | WO 2011131615 A1 * | 10/2011 | C07D 231/16 |

OTHER PUBLICATIONS

Pazenok et al. "Process for preparing 5-fluoro-1-alkyl-3-fluoroalkyl-1H-pyrazole-4-carbonyl chlorides and fluorides" WO 2011/131615 A1 (Oct. 27, 2011) English machine translation obtained from the Internet at <https://patents.google.com/>.*
Sasson et al. Chem. Commun. "Tetramethylammonium chloride as a selective and robust phase transfer catalyst in a solid-liquid halex reaction: the role of water" 1996, 297-298.*
International Search Report in corresponding International Application No. PCT/EP2014/050767 dated Feb. 19, 2014.

* cited by examiner

*Primary Examiner* — Amanda L Aguirre
(74) *Attorney, Agent, or Firm* — Morrison & Foerster LLP

(57) ABSTRACT

The present invention relates to a novel process for preparing 5-fluoro-1-methyl-3-difluoromethyl-1H-pyrazole-4-carbaldehyde, a useful intermediate in the manufacture of fungicides.

6 Claims, No Drawings

PROCESS FOR PREPARING 5-FLUORO-1-METHYL-3-DIFLUOROMETHYL-1H-PYRAZOLE-4-CARBALDEHYDE

CROSS-REFERENCE TO RELATED APPLICATION(S)

The present application is a 35 U.S.C. § 371 national phase conversion of PCT/EP2014/050767 filed on Jan. 16, 2014, which claims priority of European Application No. 13151564.5 filed on Jan. 17, 2013. Applicants claim priority to each of the foregoing applications. The PCT International Application was published in the English language.

FIELD OF THE INVENTION

The present invention relates to a novel process for preparing 5-fluoro-1-methyl-3-difluoromethyl-1H-pyrazole-4-carbaldehyde (I), a useful intermediate in the manufacture of fungicides.

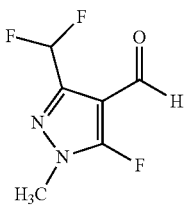

(I)

BACKGROUND OF THE INVENTION

Processes for exchanging chlorine for fluorine (halex processes) are known particularly for 5-chloro-1,3-dialkyl-1H-pyrazole-4-carbonyl chlorides (cf. for example WO 2007/031212 and EP-A 0 776 889). It is also known from WO 2011/061205 that 5-fluoro-1-alkyl-3-fluoroalkyl-1H-pyrazole-4-carbonyl chlorides can be prepared by reacting in a first step 5-chloro-1-alkyl-3-fluoroalkyl-1H-pyrazole-4-carbaldehyde with metal fluorides like KF as fluorinating reagent to obtain 5-fluoro-1-alkyl-3-fluoroalkyl-1H-pyrazole-4-carbaldehyde, followed by a second reaction with a chlorinating agent to obtain the acyl chloride derivatives.

SUMMARY OF THE INVENTION

It has now been found that the fluorination occurring in the preparation of 5-fluoro-1-methyl-3-difluoromethyl-1H-pyrazole-4-carbaldehyde from 5-chloro-1-methyl-3-difluoromethyl-1H-pyrazole-4-carbaldehyde can be significantly and surprisingly accelerated and improved by the utilization of a phase transfer catalyst selected among tetrabutylammonium chloride, bromide or hydrogen sulphate in dimethylformamide or dimethylacetamide as solvent. Under such conditions, it is possible to reduce both the reaction time and the amount of potassium fluoride used for the fluorination, leading to a cheaper and more sustainable process.

The present invention relates to a process for preparing 5-fluoro-1-methyl-3-difluoromethyl-1H-pyrazole-4-carbaldehyde of formula (I)

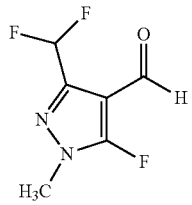

(I)

characterized in that 5-chloro-3-(difluoromethyl)-1-methyl-1H-pyrazole-4-carbaldehyde of formula (II)

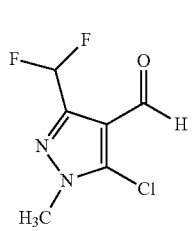

(II)

is reacted with potassium fluoride of formula (III)

$$K^+F^-$$ (III)

in the presence of a phase transfer catalyst selected among tetrabutylammonium chloride, bromide or hydrogen sulphate, preferably tetrabutylammonium hydrogen sulphate, in dimethylformamide or dimethylacetamide as solvent.

DETAILED DESCRIPTION OF THE INVENTION

The process according to the invention can be illustrated by the following formula scheme:

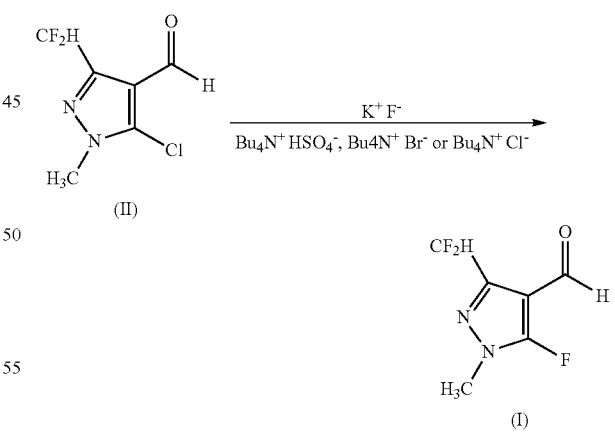

where the fluorination is performed with potassium fluoride in the presence of a phase transfer catalyst selected among tetrabutylammonium chloride, bromide or hydrogen sulphate, preferably tetrabutylammonium hydrogen sulphate, in dimethylformamide or dimethylacetamide as solvent.

5-Chloro-1-alkyl-3-fluoroalkyl-1H-pyrazole-4-carbaldehydes are known or obtainable by known methods (cf. *J. Het. Chem.* 1990, 27, 243, WO 2006/018725).

5-Chloro-1-alkyl-3-difluoroalkyl-1H-pyrazole-4-carbaldehyde of formula (II) can be prepared according to WO 2011/061205.

Potassium fluoride is a known synthesis chemical.

Reaction temperature in the process according to the invention is from 130° C. to 160° C., preferably from 145° C. to 155° C.

Reaction time is from 2 to 4 hours, preferably 3 hours.

The process according to the invention is carried out by using generally from 1 to 1.5 mol, preferably from 1.1 to 1.5 mol, of potassium fluoride per mole of 5-chloro-1-methyl-3-difluoromethyl-1H-pyrazole-4-carbaldehyde of formula (II).

The process according to the invention is carried out by using generally from 1 to 5 mol % of the phase transfer catalyst per mole of 5-chloro-1-methyl-3-difluoromethyl-1H-pyrazole-4-carbaldehyde of formula (II).

The process is preferably performed in equipment which is not a glass equipment, because KF can react under the reaction conditions with the glass equipment to produce side products ($H_2O$). Teflon or stainless steel equipment is preferable.

The process can be performed under normal atmosphere or under pressure (in closed vessel).

The potassium fluoride is generally used as a spray-dried.

PREPARATION EXAMPLES

Example 1

Preparation of 5-fluoro-1-methyl-3-difluoromethyl-1H-pyrazole-4-carbaldehyde (I) in Presence of the Catalyst Bu4N$^+$ HSO4$^-$ in dimethylacetamide

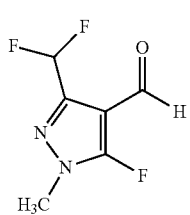

(I)

19.4 g (100 mmol) of 5-chloro-1-methyl-3-difluoromethyl-1H-pyrazole-4-carbaldehyde (II) were initially charged in 120 ml dimethylacetamide. This was followed by the addition of 6.84 g (120 mmol) of spry dried potassium fluoride and 1 g (3 mol %) of Bu4N$^+$ HSO4$^-$, heating to 150° C. and subsequent stirring at that temperature for 3 hours. GC (gas chromatography) of the reaction mixture shows 100% conversion This was followed by dilution of the mixture with toluene, filtration and removal of the solvent in vacuo at 1 mbar and 70° C. to obtain 18.5 g of 5-fluoro-1-methyl-3-difluoromethyl-1H-pyrazole-4-carbaldehyde having a purity w.w. % of 90.

$^1$H NMR (CD3CN): δ=9.8 (1H, s), 6.88 (1H, t), 3.7 (3H, s) ppm.

$^{19}$F NMR (CD3CN): δ=−114.75 (2F, t), −124.06 (1F, s) ppm.

Example 2

The reaction was performed similar to example 1 but without the catalyst Bu4N$^+$ HSO4$^-$. In these conditions, GC of the reaction mixture shows 55% of conversion after 3 hours, 65% of conversion after 6 hours, 75% of conversion after 9 hours and 78% of conversion after 15 h.

Example 3

Preparation of 5-fluoro-1-methyl-3-difluoromethyl-1H-pyrazole-4-carbaldehyde (I) in Presence of the Catalyst Bu4N$^+$ HSO4$^-$ in dimethylformamide 19.4 g (100 mmol) of 5-chloro-1-methyl-3-difluoromethyl-1H-pyrazole-4-carbaldehyde (II-1) were initially charged in 120 ml dimethylformamide. This was followed by the addition of 6.84 g (120 mmol) of spry dried potassium fluoride and 1 g (3 mol %) of Bu4N$^+$ HSO4$^-$, heating to 150° C. and subsequent stirring at that temperature for 3 hours. GC of the reaction mixture shows 100% conversion. This was followed by dilution of the mixture with toluene, filtration and removal of the solvent in vacuo at 0.5 mbar and 70° C. to obtain 18.3 g of 5-fluoro-1-methyl-3-difluoromethyl-1H-pyrazole-4-carbaldehyde having a purity w.w. % of 92.

Example 4

The reaction was performed similar to example 3, but without the catalyst Bu4N$^+$ HSO4$^-$. In these conditions, GC of the reaction mixture shows 52% of conversion after 3 hours, 73% of conversion after 6 hours, 83% of conversion after 9 hours and 93% of conversion after 15 h.

Example 5

Preparation of 5-fluoro-1-methyl-3-difluoromethyl-1H-pyrazole-4-carbaldehyde (I) in Presence of the Catalyst Bu4N$^+$ HSO4$^-$ in dimethylformamide 19.4 g (100 mmol) of 5-chloro-1-methyl-3-difluoromethyl-1H-pyrazole-4-carbaldehyde (II-1) were initially charged in 120 ml dimethylformamide. This was followed by the addition of 6.27 g (110 mmol) of spry dried potassium fluoride and 1 g (3 mol %) of Bu4N$^+$ HSO4$^-$, heating to 150° C. and subsequent stirring at that temperature for 3 hours. GC of the reaction mixture shows 99% conversion. This was followed by dilution of the mixture with toluene, filtration and removal of the solvent in vacuo at 1 mbar and 70° C. to obtain 18.1 g of 5-fluoro-1-methyl-3-difluoromethyl-1H-pyrazole-4-carbaldehyde having a purity w.w. % of 89.

Example 6

The reaction was performed similar to experiment 5, but without the catalyst Bu4N$^+$ HSO4$^-$. In these conditions, GC of the reaction mixture shows 35% of conversion after 3 hours, 50% of conversion after 6 hours, and 65% of conversion after 15 h.

Example 7

Preparation of 5-fluoro-1-methyl-3-difluoromethyl-1H-pyrazole-4-carbaldehyde (I) in Presence of the Catalyst Bu4N$^+$ Br$^-$ in dimethylformamide 19.4 g (100 mmol) of 5-chloro-1-methyl-3-difluoromethyl-1H-pyrazole-4-carbaldehyde (II-1) were initially charged in 120 ml dimethylformamide. This was followed by the addition of 6.27 g (110 mmol) of spry dried potassium fluoride and 0.96 g (3 mol %) of Bu4N⁺ Br⁻, heating to 150° C. and subsequent stirring at that temperature for 3 hours. GC of the reaction mixture shows 98% conversion. This was followed by dilution of the mixture with toluene, filtration and removal of the solvent in vacuo at 0.5 mbar and 70° C. to obtain 17.8 g of 5-fluoro-1-methyl-3-difluoromethyl-1H-pyrazole-4-carbaldehyde having a purity w.w. % of 89.

Example 8

Preparation of 5-fluoro-1-methyl-3-difluoromethyl-1H-pyrazole-4-carbaldehyde (I) in dimethylacetamide 19.4 g (100 mmol) of 5-chloro-1-methyl-3-difluoromethyl-1H-pyrazole-4-carbaldehyde (II-1) were initially charged in 120 ml dimethylacetamide. This was followed by the addition of 8.55 g (150 mmol) of spry dried potassium fluoride, heating to 150° C. and subsequent stirring at that temperature for 3 hours. GC shows only 55% conversion.

The invention claimed is:
1. A process for preparing 5-fluoro-1-methyl-3-difluoromethyl-1H-pyrazole-4-carbaldehyde of formula (I)

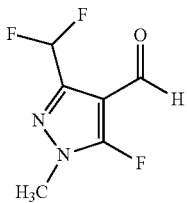

(I)

characterized in that 5-chloro-3-(difluoromethyl)-1-methyl-1H-pyrazole-4-carbaldehyde of formula (II)

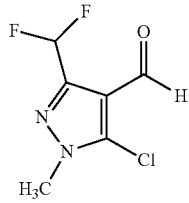

(II)

is reacted with potassium fluoride of formula (III)

K⁺F⁻     (III)

in the presence of a phase transfer catalyst selected from the group consisting of tetrabutylammonium chloride, tetrabutylammonium bromide and tetrabutylammonium hydrogen sulphate in dimethylformamide or dimethylacetamide as solvent.

2. The process according to claim 1 wherein the phase transfer catalyst is tetrabutylammonium hydrogen sulphate.

3. The process according to claim 1 wherein the reaction temperature is from 130° C. to 160° C.

4. The process according to claim 1 wherein the reaction time is from 2 to 4 hours.

5. The process according to claim 1 wherein from 1 to 1.5 mol of potassium fluoride per mole of 5-chloro-1-methyl-3-difluoromethyl-1H-pyrazole-4-carbaldehyde of formula (II) is used.

6. The process according to claim 1 wherein from 1 to 5 mol % of the catalyst per mole of 5-chloro-1-methyl-3-difluoromethyl-1H-pyrazole-4-carbaldehyde of formula (II) is used.

* * * * *